United States Patent [19]

Fernandes et al.

[11] Patent Number: 4,992,271

[45] Date of Patent: Feb. 12, 1991

[54] FORMULATION FOR LIPOPHILIC IL-2 PROTEINS

[75] Inventors: Peter M. Fernandes, Walnut Creek; Terrance Taforo, Oakland, both of Calif.

[73] Assignee: Cetus Corporation, Emeryville, Calif.

[21] Appl. No.: 775,751

[22] Filed: Sep. 13, 1985

Related U.S. Application Data

[60] Continuation-in-part of Ser. No. 752,403, Jul. 5, 1985, which is a continuation-in-part of Ser. No. 592,077, Mar. 23, 1984, abandoned, which is a division of Ser. No. 495,896, May 18, 1983, Pat. No. 4,462,940, which is a continuation-in-part of Ser. No. 422,421, Sep. 23, 1982, abandoned.

[51] Int. Cl.$^5$ .................. A61K 37/02; A61K 45/02
[52] U.S. Cl. .................. 424/85.2; 424/85.1; 424/85.4; 424/85.5; 424/85.6; 424/85.7; 424/85.91; 514/2; 514/8; 514/21; 514/885; 514/970; 514/12; 530/351; 435/811
[58] Field of Search .............. 424/85, 85.1, 85.2; 514/2, 8, 21, 12, 885; 530/351; 435/811

[56] References Cited

U.S. PATENT DOCUMENTS

| | | | |
|---|---|---|---|
| 4,289,689 | 9/1981 | Friesen et al. | 424/85 |
| 4,315,852 | 2/1982 | Leibowitz et al. | 424/85 |
| 4,343,735 | 8/1982 | Menge et al. | 424/85 |
| 4,343,736 | 8/1982 | Uemura et al. | 424/85 |
| 4,364,863 | 12/1982 | Leibowitz et al. | 424/85 |
| 4,390,623 | 6/1983 | Fabricius et al. | 435/68 |
| 4,401,756 | 8/1983 | Gillis | 435/68 |
| 4,448,879 | 5/1984 | Fabricius et al. | 435/2 |
| 4,450,103 | 5/1984 | Konrad et al. | 424/85 |
| 4,460,574 | 7/1984 | Yabrov | 424/85 |
| 4,462,940 | 7/1984 | Hanisch et al. | 424/85 |
| 4,464,355 | 8/1984 | Fabricius et al. | 424/101 |
| 4,490,289 | 12/1984 | Stern | 530/351 |
| 4,508,833 | 4/1985 | Sonneborn et al. | 530/351 |
| 4,530,787 | 7/1985 | Shaked et al. | 530/351 |
| 4,569,790 | 2/1986 | Koths et al. | 530/351 |
| 4,572,798 | 2/1986 | Koths et al. | 530/351 |
| 4,604,284 | 8/1986 | Kung et al. | 530/351 |
| 4,604,377 | 8/1986 | Fernandes et al. | 514/8 |
| 4,645,830 | 2/1987 | Yasushi et al. | 530/351 |
| 4,659,570 | 4/1987 | Terano | 424/85 |
| 4,738,927 | 4/1988 | Taniguchi et al. | 435/243 |
| 4,748,234 | 5/1988 | Dorin et al. | 530/412 |
| 4,778,879 | 10/1988 | Mertelsmann et al. | 530/351 |
| 4,789,658 | 12/1988 | Yoshimoto et al. | 514/2 |
| 4,812,557 | 3/1989 | Yasushi et al. | 530/351 |

FOREIGN PATENT DOCUMENTS

| | | |
|---|---|---|
| 0042246 | 12/1981 | European Pat. Off. |
| 0080879 | 6/1983 | European Pat. Off. |
| 0089245 | 9/1983 | European Pat. Off. |
| 0092163 | 10/1983 | European Pat. Off. |
| 0118617 | 9/1984 | European Pat. Off. |
| 0118997 | 9/1984 | European Pat. Off. |
| 0119621 | 9/1984 | European Pat. Off. |
| 0145390 | 6/1985 | European Pat. Off. |
| 0147819 | 7/1985 | European Pat. Off. |
| 0158487 | 10/1985 | European Pat. Off. |
| 0162332 | 11/1985 | European Pat. Off. |
| 0229016 | 7/1987 | European Pat. Off. |
| 80/02229 | 10/1980 | PCT Int'l Appl. |

OTHER PUBLICATIONS

Mieu et al., *J. Immunol.*, 128(3), 1982, pp. 1122–1127.
Mieu et al., *Lymphokine*, vol. 6, 1982, pp. 137–163.

(List continued on next page.)

Primary Examiner—Garnette Draper
Attorney, Agent, or Firm—Janet E. Hasak; Jane R. McLaughlin; Albert P. Halluin

[57] ABSTRACT

An improved process for recovering and purifying lipophilic recombinant proteins such as human β-interferon and interleukin-2 from their hosts yields a protein preparation which may be formulated into a stable pharmaceutical composition having a therapeutically effective amount of the biologically active recombinant lipophilic protein dissolved in a non-toxic, inert, therapeutically compatible aqueous-based carrier medium at a pH of 6.8 to 7.8 which medium also contains a stabilizer for the protein, such as human serum albumin, normal serum albumin and human plasma protein fraction.

8 Claims, 6 Drawing Sheets

OTHER PUBLICATIONS

Acuto et al., *J. Immunological Methods*, 53, 1982, pp. 15–26.
Caplan et al., 1981, *J. Immunol.*, 26:1351–1354.
Welte et al., 1982, *J. Exp. Med.*, 156:454.
Henriksen, O. et al., 1982, *Cellular Immunol.*, 73:106–114.
Doyle, M. V. et al., 1985, J. Biol. Res. Mod., 4:96–109.
Robb, R. J., 1984, *Immunol. Today*, 5(7):203–209.
Robb, R. J. et al., 1981, *Mol. Immunol.*, 18:1087–1094.
Robb, R. J. et al., 1983, *Proc. Natl. Acad. Sci.*, 80:5990–5994.
Sofer, "Chromatographic Removal of Pyrogens", *Bio/Technol.*, Dec. 1984:1035–1038.
Mochizuki et al., 1980, *J. Immunol. Meth.*, 39:185–201.
Gillis, S. et al., 1980, *J. Immunol.*, 124:1954–1962.
Berman et al., 1985, *Trends in Biochemistry*, 3(2):51–53.
Wang, Y.-C. J. et al., 1988, *J. Parenteral Sci. and Technol.*, 42:S3–S26.
Stern et al., 1984, *Immunol.*, 81:871–875.
Mertelsmann et al., 1984, *J. Biol. Response Modifiers*, 4:483–490.
Taniguchi et al., *Nature*, 302, 1983, pp. 305–310.
Rosenberg et al., *Science*, 223, 1984, pp. 1412–1415.
Devas et al., *Nucleic Acid Res.*, 11(13), 1983, pp. 4306–4323.
Sakamoto et al., CA, vol. 104, 1986, #205522j.
*Cancer Treatment Reports*, vol. 62, No. 11, Nov. 1978, pp. 1900–1906.
Symbalista, Samuel, *Chem. Abs.*, vol. 99, p. 353, (181455g), (1983), referring to EP 89,245, pub. 9/21/83.
Kwan, Henry, *Chem. Abs.*, vol. 99, (76913g), (1983), referring to EP 82,481, publ. 6/29/83.

FERMENTATION
|
CELL CONCENTRATION
|
CELL MEMBRANE DISRUPTION ——— DISTILLED WATER
|
DIAFILTRATION ——————— 5 mM EDTA
|
REDISRUPTION ——————— 2 mM EDTA 1% OCTANOL(v/v)
|
SUCROSE SUSPENSION ——————— 15-35% SUCROSE (w/w)
|
CENTRIFUGATION ——————— 10,000-20,000 x g
|
SOLUBILIZATION ——————— 5% SDS, PHOSPHATE BUFFERED SALINE
|
CENTRIFUGATION ——————— 25,000-35,000 x g
|
REDUCTION ——————— 5% SDS, 50 mM DTT, 2 mM EDTA pH 8.5 AT 50°C FOR 20 MINUTES
|
SEPHACRYL S-200-A COLUMN ——— 50 mM ACETATE, pH 5.5, 0.1% SDS, 1 mM EDTA
|
OXIDATION ——————— IODOSOBENZOIC ACID (IBA) 1:1.6 MOLAR PROTEIN:IBA, 0.1% SDS, 10 mM PHOSPHATE, pH 7.8, 1 mM EDTA

FIG. 5(a)

| CONCENTRATION | pH 5.5 |
| DIAFILTRATION | 0.1% SDS, ImM EDTA, 50 mM ACETATE pH 5.5 |
| FILTRATION | pH _3, 0.45 μm FILTER |
| PREPARATIVE RP-HPLC | Vydac C-4 BONDED PHASE SILICA GEL, 2 PROPANOL/ACETIC ACID |
| DILUTION | 1:14 INTO 50 mM ACETATE, pH 5.5, 1.0% SDS, 1 mM EDTA |
| CONCENTRATION | |
| DIAFILTRATION | 50 mM ACETATE pH 5.5, 0.1% SDS, 1 MM EDTA |
| SEPHACRYL S-200-B COLUMN | 50 mM ACETATE pH 5.5 0.1% SDS, 1mM EDTA |
| DESALTING | G25 SEPHADEX COLUMN AT pH 9.2-11 |
| pH ADJUSTMENT | SEPARATELY ADJUST pH OF PROTEIN AND HSA OR PPF TO 2-4 |
| FORMULATION | 2.5% HSA OR PPF (w/v), pH 2-4 |
| INCUBATION | 15 MINUTES |
| pH ADJUSTMENT | pH 7.5 |
| FILTRATION | |
| LYOPHILIZATION | |

FIG. 5(b)

FORMULATION FOR LIPOPHILIC IL-2 PROTEINS

This application is a continuation-in-part application of copending U.S. Serial No. 752,403 filed July 5, 1985, which is a continuation-in-part application of U.S. Ser. No. 592,077 filed Mar. 23, 1984, now abandoned which is a divisional application of U.S. Ser. No. 495,896 filed May 18, 1983, issued as U.S. Pat. No. 4,462,940 on July 31, 1984, which is a continuation-in-part application of U.S. Ser. No. 422,421, filed Sept. 23, 1982, now abandoned. This application is also related to U.S. Ser. No. 353,360, filed Mar. 1, 1982, issued as U.S. Pat. No. 4,450,103 on May 22, 1984.

BACKGROUND OF THE INVENTION

This invention is in the general field of biochemical engineering. More specifically, the subject invention relates to the preparation of biologically active recombinant lipophilic proteins such as human interferons and interleukin-2. Still more specifically, the subject invention relates to an improved process for the production and recovery of lipophilic proteins from genetically transformed host organisms, lipophilic protein preparations of relatively high purity, and therapeutically acceptable formulations thereof.

Interleukin-2 (IL-2) is a lymphokine which is produced by normal peripheral blood lymphocytes and induces proliferation of antigen or mitogen stimulated T cells after exposure to plant lectins, antigens, or other stimuli. IL-2 was first described by Morgan, D. A., et al., Science (1976) 193:1007–1008 and was then designated T cell growth factor because of its ability to induce proliferation of stimulated T lymphocytes. Now renamed as interleukin-2, IL-2 later has been found also to modulate a variety of functions of immune system cells in vitro and in vivo. IL-2 is one of several lymphocyteproduced messenger-regulatory molecules which mediate immunocyte interactions and functions.

IL-2 was initially made by cultivating human peripheral blood lymphocytes (PBL) or other IL-2-producing cell lines. See, for example, U.S. Pat. No. 4,401,756. Recombinant DNA technology has provided an alternative to PBLs and cell lines for producing IL-2. Taniguchi, T., et al., Nature (1983) 302:305–310 and Devos, R., Nucleic Acids Research (1983) 11:4307–4323 have reported cloning the human IL-2 gene and expressing it in microorganisms.

Naturally occurring interferons (IFNs) are species-specific proteins, often glycoproteins, produced by various cells upon induction with viruses, double stranded RNA's, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

Native human $\beta$-interferon ($\beta$-HIFN) is generally produced by superinducing human fibroblast cultures with poly-IC (polyriboinosinic acid and polyribocytidylic acid) and isolating and purifying the $\beta$-HIFN thus produced by chromatographic and electrophoretic techniques. Proteins or polypeptides which exhibit native $\beta$-interferon like properties may also be produced using recombinant DNA technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the $\beta$-HIFN therefrom. Nagola, S. et al., Nature, 284:316 (1980); Goeddel, D. V. et al., Nature, 287:411 (1980); Yelverton, E. et al., Nuc. Acid Res., 9:731 (1981); Streuli, M. et al., Proc. Nat'l. Acad. Sci. (U.S.), 78:2848 (1981); European Pat. Application Numbers 28033, published May 6, 1981; 321134, published July 15, 1981; 34307 published Aug. 26, 1981; and Belgian Patent 837397, issued June 1, 1981 describe various currently used methods for the production of $\beta$-interferon employing recombinant DNA techniques. The expressed proteins or polypeptides have been purified and tested and have been found to exhibit properties similar to those of native IFNs. Bacterially produced IFN's thus appear to have potential therapeutic use as anti-viral and anti-tumor agents and the production of IFN's by such bacterial fermentations is expected to yield sufficiently large quantities of IFN at a relatively low cost for clinical testing.

Protein samples for use in clinical studies, however, rust be of relatively high purity and substantially uncontaminated with toxic host cell constituents, cell debris and other extraneous chemicals introduced during the extraction and purification steps. There are several methods currently available for the preparation, recovery and purification of bacterially produced proteins.

U.S. Pat. No. 4,315,852 to Leibowitz et al. describes and claims a method for the acid extraction of leukocyte interferon from bacterial cells and neutralization of the extractant to obtain the interferon.

Derynck et al., Nature, 287:193 (1980) teach lysing transformed E. coli cells using a solution containing 5M urea, 1% sodium dodecyl sulfate (SDS), and 1% 2-mercaptoethanol. The lysate, which was purified by chromatography, exhibited interferon activity.

Scandella and Kornberg, Biochemistry, 10:4447 (1971) describe the preparation of a phospholipase from E. coli by solubilizing the cell membranes with SDS and precipitating the solubilized protein with 1-butanol.

U.S. Pat. No. 4,343,735, to Menge et al. teaches a process for the purification of interferon by partitioning it in an aqueous multi-phase system in the presence of ion exchangers which are soluble in the system and are derivatives of polyethers.

U.S. Pat. No. 4,343,736 to Uemura et al. discloses a method for recovering interferon by absorption on water-insolubilized heparin and then eluting the interferon with an aqueous solution of an inorganic salt and chondroitin sulfate.

U.S. Pat. No. 4,289,689 to Friesen et al. discloses how to recover and purify human native $\beta$-interferon by use of affinity chromatography and high pressure liquid chromatography.

U.S. Pat. No. 4,460,574 to Yabrov discloses a pharmaceutical composition comprising native human and$\alpha$- and $\beta$-interferons used for rectal or urogenital treatment of human interferon-sensitive diseases.

U.S. Pat. No. 4,364,863 to Leibowitz et al. describes a method of extracting fibroblast interferon from bacteria using a low pH followed by a high pH extraction procedure.

PCT WO 80/02229 to Benzon discloses purification of alpha (leukocyte) interferon, which is not a lipophilic protein.

EP 42,246 discloses that recombinant interferons may be dissolved in any pharmaceutically acceptable non-toxic carrier appropriate for the desired form of administration without further details.

U.S. Pat. No. 4,450,103 discloses solubilizing the protein in an aqueous medium with an appropriate solubilizing agent, extracting the protein from the aqueous medium with 2-butanol or 2-methyl-2-butanol, and precipitating the protein from the alcohol phase.

*Cancer Treatment Reports*, 62, 1900–1906 (1978) and EP 89,245 disclose that native beta-interferon may be formulated directly with human serum albumin in a pharmaceutically compatible aqueous-based medium at a pH of 7.2–7.8.

Alpha-interferons and native beta-interferon are not lipophilic proteins. Therefore, they can be stabilized and solubilized by adding a stabilizer such as human serum albumin directly to the formulation at physiological pH. In contrast, lipophilic proteins such as recombinant beta-interferon and interleukin-2 are not solubilized by addition of human serum albumin at pH 6.8–7.8.

A major problem with the existing methods of purification and recovery of lipophilic proteins is that the protein is not produced in a sufficiently pure form and in sufficiently large quantities for clinical and therapeutic purposes, and further, that the resulting protein preparations, especially those that are produced by recombinant DNA techniques, have residual toxic amounts of chemicals, such as SDS and other surfactants or precipitants used in the extraction and purification steps. Thus, these preparations are not acceptable for clinical studies designed to determine the extent of the therapeutic use and applications of these proteins. It would be desirable, therefore, to have available a process for the recovery of a lipophilic protein in sufficiently large quantities and without toxic levels of SDS for clinical and therapeutic applications.

Applicants have heard of a disclosure in early 1985 of low pH formulation of proteins, but have no evidence thereof.

Accordingly, it is an object of the present invention to provide a pharmaceutically acceptable sample of a lipophilic protein such as recombinant β-interferon or interleukin-2 which is of relatively high purity.

Another object of the present invention is to provide pharmaceutically acceptable samples of lipophilic proteins such as recombinant β-interferon or interleukin-2 in sufficiently large quantities for clinical and therapeutic applications.

Yet another object of the instant invention is to provide lipophilic proteins such as recombinant β-interferon or interleukin-2 preparations which are substantially free of SDS without loss of their biological activity, or at levels that are therapeutically acceptable.

A further object of this invention is to provide recombinant β-interferon and interleukin-2 samples wherein the level of SDS is less than about 10 p.p.m.

SUMMARY OF THE INVENTION

To achieve the foregoing and other objects and in accordance with the purpose of the present invention, as embodied and broadly described herein, one aspect of the invention is an improved method for the production, recovery and purification of a lipophilic protein such as human recombinant β-interferon and interleukin-2 and comprises solubilizing the protein into an aqueous medium with a suitable solubilizing agent, extracting the solubilized protein with an aliphatic alcohol, precipitating the protein from the alcohol phase with an aqueous buffer, and diafiltering the protein at a pH of about 10.5 to 12.5, preferably at a pH of about 12, against water adjusted to a pH of about 10.5 to 12.5, preferably about 12, or against mixtures of water and aliphatic alcohols, preferably ethanol and glycerol adjusted to a pH of about 10.5 to 12.5, preferably about 12, substantially to remove SDS or to reduce its concentration to therapeutically acceptable levels. The protein sample is optionally purified by conventional methods such as chromatography prior to the diafiltration.

A preferred embodiment of the above method comprises recovering bacterially produced human β-interferon by disruption of the bacterial cells, solubilization of the interferon with a suitable solubilizing agent, extracting the solubilized interferon with an aliphatic alcohol of 2–6, preferably 4–6 carbon chain length, precipitating the interferon from the alcohol phase, further purifying the interferon by conventional methods, preferably gel filtration chromatography, and diafiltering the interferon fraction at a pH of about 10.5 to 12.5, preferably at a pH of about 11, against pure water or mixtures of water and aliphatic alcohols, preferably methanol, ethanol, propanol, butanol, glycerol and the like, also adjusted to a pH of about 10.5 to 12.5, preferably about 11.

Another aspect of the present invention deals with an improved process for the recovery of human β-interferon and a therapeutic formulation thereof where the levels of SDS are less than about 10 p.p.m.

In another aspect, the therapeutic formulation is a stable pharmaceutical composition comprising a therapeutically effective amount of a biologically active recombinant lipophilic protein dissolved in a non-toxic, inert, therapeutically compatible aqueous-based carrier medium at a pH of 6.8 to 7.8 comprising a stabilizer for the protein.

Preferably, the protein in this latter formulation is β-interferon or interleukin-2 and the stabilizer is human serum albumin, a mixture of human serum albumin and dextrose, human plasma protein fraction, or normal serum albumin.

In a further aspect of the present invention, the therapeutic protein preparation obtained from the diafiltration and stabilization steps may be lyophilized and reconstituted in an inert, non-toxic, physiologically compatible carrier medium for therapeutic and clinical applications.

BRIEF DESCRIPTION OF THE DRAWINGS

FIG. 6 illustrates a flow chart of the process steps of the present invention wherein the protein is extracted and solubilized and the pH is lowered to acidic pH for stabilizer addition.

DETAILED DESCRIPTION OF THE PREFERRED EMBODIMENTS

As used herein, the term "lipophilic protein" refers to a protein which is not soluble or not readily soluble in an aqueous medium under ambient conditions of room temperature and atmospheric pressure at a pH of between about 6.5 and 7.8. Examples of such proteins include human recombinant $\beta$-interferon, recombinant interleukin-2 and immunotoxins prepared by conjugating a cytotoxin moiety such as ricin A to an antibody against a pathologic condition such as breast cancer. The term "recombinant protein" refers to a protein which is produced by recombinant DNA techniques wherein generally DNA is inserted into a suitable expression plasmid which is inserted into a host organism not native to the DNA which is transformed to produce the heterologous protein. The host may be any organism foreign to the DNA such as, e.g., bacteria, yeast, viruses, mammals, etc. Preferably the host is microbial, and most preferably is bacterial.

As used herein, the term "$\beta$-HIFN" refers to human $\beta$-interferon or $\beta$-interferon-like polypeptides produced by recombinant DNA techniques and whose amino acid sequence is the same as or similar or substantially homologous to the unglycosylated and/or glycosylated native $\beta$-interferon.

As used herein the term "IL-2" refers to human interleukin-2 or interleukin-2-type polypeptides produced by recombinant DNA techniques and whose amino acid sequence is the same as or similar or substantially homologous to the unglycosylated and/or glycosylated native interleukin-2.

The precise chemical structure of the protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Finally, modifications to the primary structure itself by deletion, addition, or alteration of the amino acids incorporated into the sequence during translation can be made without destroying the activity of the protein. For example, at least one cysteine residue which is not essential to biological activity, is present in the biologically active protein, and is free to form a disulfide link may be deleted or replaced with another amino acid to eliminate sites for intermolecular crosslinking or incorrect intramolecular disulfide bond formation. Such modified proteins, known as "muteins," are described in U.S. Pat. No. 4,518,584 issued May 21, 1985. In another example, a conservative amino acid of a biologically active protein such as IL-2 or IFN-$\beta$ is substituted for each methionine residue susceptible to chloramine T or peroxide oxidation, wherein additional, nonsusceptible methionine residues are not so substituted. A conservative amino acid alteration in this context is defined as one which does not adversely affect biological activity and involves neutral or non-polar amino acid substitutions or deletion of the methionine. In a preferred example of this embodiment the methionine at amino acid position 104 of IL-2 is replaced by an alanine residue.

Preferably the protein herein is $\beta$-HIFN or IL-2. Most preferably the protein is unglycosylated $\beta$-HIFN or IL-2 which is produced by a microorganism that has been transformed with a human IFN-$\beta$ or IL-2 gene or a modification of the human IFN-$\beta$ or IL-2 gene that encodes a protein having: (a) an amino acid sequence that is at least substantially identical to the amino acid sequence of native human IFN-$\beta$ or IL-2 and (b) biological activity that is common to native human IFN-$\beta$ or IL-2. Substantial identity of amino acid sequences means the sequences are identical or differ by one or more amino acid alterations (deletions, additions, substitutions) that do not cause an adverse functional dissimilarity between the synthetic protein and the native human IFN-$\beta$ or IL-2. Examples of such proteins are the IFN-$\beta$ or IL-2 proteins described in U.S. Pat. No. 4,518,584. Most preferably, the IFN-$\beta$ is ser$_{17}$IFN-$\beta$ wherein the cysteine residue at amino acid position 17 is replaced by a serine residue, and the IL-2 is des-ala-ser$_{125}$ IL-2 wherein the initial alanine residue is deleted and the cysteine residue at amino acid position 125 is replaced by a serine residue.

As used herein, the term "physiological pH" refers to a pH which is pharmaceutically acceptable to mammals, i.e., a pH of about 7.2-7.6.

As used herein, the term "stabilizer" as applying to the lipophilic protein refers to non-toxic, non-therapeutic, non-immunogenic compositions which act not only to stabilize the diafiltered protein against denaturation and loss of biological activity, but also to solubilize the lipophilic protein in an aqueous medium so that the pharmaceutical formulation constitutes an aqueous solution of diafiltered protein at pH 6.8-7.8 from which the protein will not precipitate. Such stabilizers are not known in the art for their solubilizing function. Examples of such stabilizers include, but are not limited to, proteins or carbohydrates preferably chosen from the proteins human serum albumin (HSA), and human plasma protein fraction (PPF), and the carbohydrates mannitol, sorbitol, glycerol, dextrose or a mixture thereof.

The type of stabilizer employed and the concentration thereof will depend mainly on the pH method and formulation employed and on the protein. For example, HSA, or a mixture of HSA and dextrose is preferred for high pH formulations and formulations treated at low pH using a mutein of IL-2. However, for low pH formulations using IFN-$\beta_{ser17}$, PPF is preferred. PPF is commercially available and is composed of at least 83% albumin and no more than 17% globulins ($\alpha$ and $\beta$); no more than 1% of the proteins are gamma-globulins. The $\alpha$- and $\beta$-globulins in blood plasma serve several functions, one of which is to hold in stable aqueous solution relatively insoluble blood components, including cholesterol, fat-soluble vitamins, and hormones. Carbohydrate stabilizers can only be used in formulations maintained/lyophilized at pH 2-4.

The final concentration of stabilizer generally may range from 0.1-10% (w/v) depending mainly on the protein and type of stabilizer and the pH employed, with higher ranges preferred for low pH. A range of 0.5 to 10% (w/v) is typical for HSA with $\beta$-HIFN; 0.1 to 5% (w/v) is typical for PPF with $\beta$-HIFN and IL-2; and 0.5-10% (w/v) is typical for HSA with IL-2.

Many of the methods used for the recovery of lipophilic recombinant proteins, such as bacterially produced $\beta$-HIFN, utilize SDS or similar surfactants for the solubilization and isolation of the protein from cellular material and subsequent acid precipitation to obtain the protein. By further purification techniques carried out at or near neutral pH, the SDS levels in the final protein preparations are reduced to about 0.1%, but even these residual levels have been found to be toxic in animal studies and thus not acceptable for therapeutic or clinical applications. Further removal of SDS by diafiltration techniques in the 4-8 pH range results in almost complete loss of $\beta$-HIFN activity due to aggregation and precipitation of the protein. The biological activity of $\beta$-HIFN lost during diafiltration may be regained by the addition of SDS.

For a free or unbound solute, the removal rate during diafiltration from a well mixed vessel follows first order kinetics. Since unbound SDS below its critical micelle concentration is a molecule small enough to pass unhindered through a 10,000 dalton cut-off membrane, its removal rate would be expected to follow first order kinetics, and if that were the case, SDS at an initial concentration of about 1000 $\mu$g/ml should be reduced to less than 1 $\mu$g/ml after about seven volume replacements. It was found, however, that SDS removal from $\beta$-HIFN did not fit this theoretical model, indicating that there were protein-SDS interactions which significantly affected the kinetics of SDS removal, and that SDS removal from this bound state in the 4–8 pH range promoted protein-protein interactions resulting in aggregation or precipitation of the protein. Higher or lower pH ranges for SDS removal would not be expected to be desirable, as at higher or lower pH, some proteins are known to be denatured. However, according to the present invention, following the removal of SDS by diafiltration at low ionic strength or by desalting, increasing or decreasing the pH by the addition of base or acid, respectively, solubilizes the protein and essentially restores its biological activity in the formulation.

Thus, the present invention solves the problem of lipophilic protein aggregation and precipitation and loss of protein activity with the removal of SDS. One solution to the problem involves initially adjusting the pH to about 10.5 to 12.5 and diafiltering against distilled water or aqueous mixtures of alcohols, using a 10,000 molecular weight cut-off ultrafiltration membrane after optionally reducing a partially purified sample of the protein with dithiothreitol (DTT) or mercaptoethanol or glutathione or cysteine at about 60° C. and a pH of about 8.5 to prevent aggregation of the protein. Exemplary alcohols include ethanol, butanols, glycerol, mannitol, sorbitol, dextrose and the like.

Another solution to the problem involves initially adjusting the pH of the purified protein pool to about 2 to 4, adding the stabilizer previously adjusted to a pH of 2 to 4, optionally incubating the mixture and raising its pH to 6.8 to 7.8. Incubation time depends mainly on the type of protein, type of stabilizer, exact pH, and concentrations of protein and stabilizer, and typically ranges from 0–100 minutes, preferably 10–100 minutes, more preferably 15–60 minutes, and most preferably 15–45 minutes.

In a third, but less preferred, solution to the problem, where the pH is low, the stabilizer and protein pool are mixed together and the pH of the mixture is adjusted to 2 to 4, and the pH is raised, gradually or at once, to 6.8–7.8.

The subject invention is therefore a process for the recovery of lipophilic recombinant proteins of relatively high purity which contain lower than toxic levels of SDS and which can be reconstituted into therapeutically acceptable formulations in an appropriate carrier medium, and lipophilic protein compositions, more preferably $\beta$-HIFN or IL-2 compositions, wherein SDS levels are at less than 10 p.p.m., usually in the range of 2–6 p.p.m.

For purposes of practicing the present invention, bacteria are the preferred microorganism hosts, with *E. coli* being the most preferred.

One embodiment of the process of the instant invention is summarized below.

FIG. 1 illustrates the details of the individual process steps of the preferred embodiment of the present invention including the culture of the transformed microorganisms in an appropriate fermentation medium through the final step where the purified $\beta$-HIFN is stabilized and may then be lyophilized and reconstituted into therapeutic formulations. The individual process steps include:

(a) growing the transformed bacterial hosts in an appropriate fermentation medium;

(b) concentrating the bacteria in the fermentation medium by cross-flow filtration;

(c) mechanically homogenizing the bacteria to disrupt the cell walls of the bacteria;

(d) separating solid cellular material from the remainder of the homogenate by centrifugation;

(e) solubilizing the solid cellular material by suspending it in an aqueous solution of sodium dodecyl sulfate (SDS) at a protein to SDS ratio of about 1:3;

(f) extracting the $\beta$-HIFN from the aqueous phase with 2-butanol or 2-methyl-2-butanol or mixtures thereof by continuous cocurrent extraction;

(g) heating the 2-butanol or 2-methyl-2-butanol phase to about 60° C. for about 10 to 20 minutes; or (h) aging the 2-butanol phase overnight;

(i) centrifuging the mixture and discarding the precipitated impurities;

(j) contacting the 2-butanol or 2-methyl-2-butanol phase with an aqueous buffer and adjusting the pH of the mixture to about 5.5 to precipitate the $\beta$-HIFN;

(k) collecting the precipitated $\beta$-HIFN by centrifugation;

(l) solubilizing the β-HIFN with distilled water or with an aqueous solution of SDS at a protein to SDS ratio of about 1:3;

(m) adjusting the pH of the solution to about 9.5 and reducing the solubilized β-HIFN with dithiothreitol;

(n) purifying the reduced β-HIFN by chromatography;

(o) collecting the eluted fraction of the purified β-HIFN;

(p) further purifying the β-HIFN by gel chromatography;

(q) collecting the eluate containing the purified β-HIFN;

(r) adjusting the pH of the eluate to about 12;

(s) diafiltering the solution containing the β-HIFN at a pH of about 11 against pure water or $H_2O$-ethanol mixtures adjusted to a pH of about 11;

(t) adjusting the pH of the diafiltrate to about 12 and stabilizing (and thereby solubilizing) the β-HIFN by the addition of a 0.5–10% by weight solution of dextrose and human serum albumin adjusted to a pH of about 12, and maintaining a pH of 12 for 1–15 minutes;

(u) adjusting the pH of the solution to physiological pH;

(v) lyophilizing the β-HIFN sample, if desired; and (w) reconstituting the lyophilized β-HIFN sample, if desired.

Ten mM dithiothreitol may be optionally included in the initial solubilization step and the mixture may be heated to about 90° C. for about 10 minutes. In addition, the β-HIFN is preferably oxidized so that its cysteine residues are bridged to form cysteines, as described by U.S. Pat. No. 4,530,787 to Shaked et al., using o-iodosobenzoic acid solution or by U.S. Pat. No. 4,572,798 issued Feb. 25, 1986 to Koths et al., entitled "Method For Promoting Disulfide Bond Formation In Recombinant Proteins", using copper chloride. The disclosure of the Koths et al. patent is incorporated herein by reference.

Generally, proteins are susceptible to denaturation, peptide bond hydrolysis, hydrolysis of individual amino acids, β-elimination, racemization, formation of different amino acids and similar reactions in the high alkaline pH range; but with β-HIFN, none of the degradative reactions enumerated above are detected. On the other hand, when the protein is diafiltered at a pH of about 11, the resulting β-HIFN is pure and homogeneous and exhibits high specific activity, close to that of native β-HIFN.

In another preferred embodiment of the process of the invention, the disrupted cells are treated to isolate and purify IL-2 or β-HIFN protein, and then the following steps are carried out:

(r) desalting the protein by G25 chromatography at pH 9.2–11;

(s) adjusting the pH of the desalted pool to about 3.5;

(t) adjusting the pH of a solution of human serum albumin or plasma protein fraction to pH 3.5;

(u) adding the human serum albumin or plasma protein fraction to the desalted pool and incubating for 15–45 minutes;

(v) lyophilizing the protein sample, if desired; and (w) reconstituting the lyophilized protein sample, if desired.

In a third embodiment of the process of this invention, the disrupted cells are treated to isolate and purify IL-2 or β-HIFN protein and then the following steps are carried out:

(r) desalting the protein by G25 chromatography at pH 9.2–11;

(s) adding human serum albumin or plasma protein fraction to the desalted pool to form a mixture;

(t) lowering the pH of the mixture to 3–4;

(u) incubating the mixture for 15–45 minutes;

(v) lyophilizing the protein sample, if desired; and (w) reconstituting the lyophilized protein sample, if desired.

The detailed procedure for obtaining the protein follows.

The transformed microorganisms are grown in a suitable growth medium, typically to an optical density (OD) of at least about 10 at 680 nm, and preferably between about 50 and 100 at 680 nm. The composition of the growth medium will depend upon the particular microorganism involved. The aqueous growth medium contains compounds that fulfill the nutritional requirements of the microorganism of choice. Growth media will typically contain assimilable sources of carbon and nitrogen, energy sources, magnesium, potassium and sodium ions, and optionally amino acids and purine and pyrimidine bases. (Review of Medical Microbiology, Lange Medical Publications, 14th Ed. pp. 80–85 (1980).) Growth media for *E. coli* are well known in the art. Depending upon the particular solubilizing agent used in the invention process it may be desirable to minimize the amount of substances in the growth medium that may decrease the solubility of the solubilizing agent in water. For instance, potassiumiions affect the solubility of SDS and, therefore, should be kept to a minimum when SDS is used as a solubilizing agent in the process, or removed by diafiltration following the concentration step.

Once the culture has reached the desired cell density, the cells are optionally killed or inactivated by heating or adding to the medium a cytotoxic agent such as chloroform or toluene that may be removed easily after the cells have been killed. The cells are thereafter optionally concentrated to about 20 to 150 mg/ml, preferably 80 to 100 mg/ml (OD 40 to 300, preferably 160 to 200 at 680 nm), by cross-flow filtration, centrifugation, or other conventional methods.

Following the concentration step, the cell membranes of the microorganisms are disrupted to facilitate the solubilization of the particulate matter in the concentrate. Protein assays for biological activity indicate that much of the protein is associated with (i.e., contained in or bound to) the cell membrane. Accordingly, disruption of the cell membrane enhances the contact of the solubilizing agent with the membranes and thus increases the rate at which the interferon associated with the membrane goes into solution. Conventional cell disruption techniques such as homogenization, sonication, or pressure cycling may be used in this step of the process. A preferred method is using a bead mill or a pressure homogenizer. Either before or after the disruption, the pH of the liquid phase of the concentrate or disruptate, as the case may be, is adjusted, if necessary, to a level that facilitates dissolution of the solubilizing agent and the particulate matter in the concentrate/disruptate. The pH ray be so adjusted by adding suitable buffers or with NaOH. In most instances a pH in the range of about 7 to about 8 is preferred.

Various techniques can be used to treat the disrupted cells. In one method, after the cells have been disrupted the particulate ratter can be separated from the liquid phase of the disruptate and resuspended in an aqueous medium buffered to the optimal pH for solubilization. The protein concentration of the cell suspension after solubilization is in the range of about 2 to about 15 mg/ml, preferably 6 to 8 mg/ml.

The solubilization of the particulate cellular material, including the lipophilic recombinant protein, can be carried out concurrently with the disruption or sequentially following the disruption. It is preferably carried out as a separate step following the disruption. The solubilization is preferably carried to completion—that is, substantially all of the particulate matter (e.g., protein, lipids, nucleic acids, phospholipids) in the disruptate is dissolved into the aqueous medium. Substantially complete dissolution of the particulate ratter is achieved by adding an appropriate solubilizing agent to the aqueous suspension. Surfactants (detergents) that have a suitable hydrophobic-hydrophilic balance to solubilize the protein and which form a complex with the protein which can be extracted into the organic phase can be used in the invention. Strong natural or synthetic anionic surfactants such as alkali metal salts of fatty acids and alkali metal alkyl sulfates may be used. Such agents will usually contain 10 to 14 carbon atoms. SDS and sodium laurate are particularly preferred solubilizing agents. Examples of other solubilizing agents that can be used in the process include, but are not limited to, sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate.

The amount of solubilizing agent used in the solubilization depends upon the particular agent and the amount of protein to be solubilized. In most instances, solubilizing agent to protein weight ratios in the range of about 1:1 to 10:1 are sufficient. When SDS is used, an SDS to protein ratio of about 1:1 to about 5:1, preferably about 3:1, is used. Temperatures in the range of 15° C. to 60° C. are generally used in the solubilization. Mixing may be employed to enhance contact between the solution and particulate matter and thus decrease the time it takes to dissolve the cellular matter. The solubilization is considered complete when the solution is substantially clear. Optical densities of about 4.0 to 8.0 at 280 nm are characteristic of the end point of the solubilization process.

Following the solubilization, the ionic strength of the solution is adjusted, if necessary, to a level at which the solution and organic extractant are substantially immiscible. The ionic strength is in the range of about 0.05 to 0.15. Inorganic salts, including NaCl and/or the like, are added to the solution for this purpose. Such ionic strengths enable phase separation after the extraction. The extractants used in the process are alcohols such as 2-butanol, 2-methyl-2-butanol, or mixtures thereof. The mixtures preferably contain less than about 50% by volume of 2-methyl-2-butanol. 2-Butanol is the preferred extractant. The ability of these alcohols to extract the lipophilic protein from the solubilizate is specific. The extractant is normally combined with the aqueous solution of the protein in volume ratios in the range of about 0.8:1 to about 3:1, preferably about 1:1 (extractant:aqueous solution). The extraction can be carried out using conventional batch or continuous liquid-liquid extraction techniques and equipment. The extraction is normally carried out at about 20° C. to 100° C. and involves contact times in the range of about one minute to one hour. The optimum contact time depends upon the particular solubilizing agent and extractant combination. When SDS is used, shorter times in the above range can be used. When sodium laurate is used, longer times in the range must be used. The pH of the extraction mixture ranges between about 6 and 9, with a pH of about 7.5 being preferred when SDS is used, and a pH of about 8.5 when sodium laurate is used.

Figure 1A:
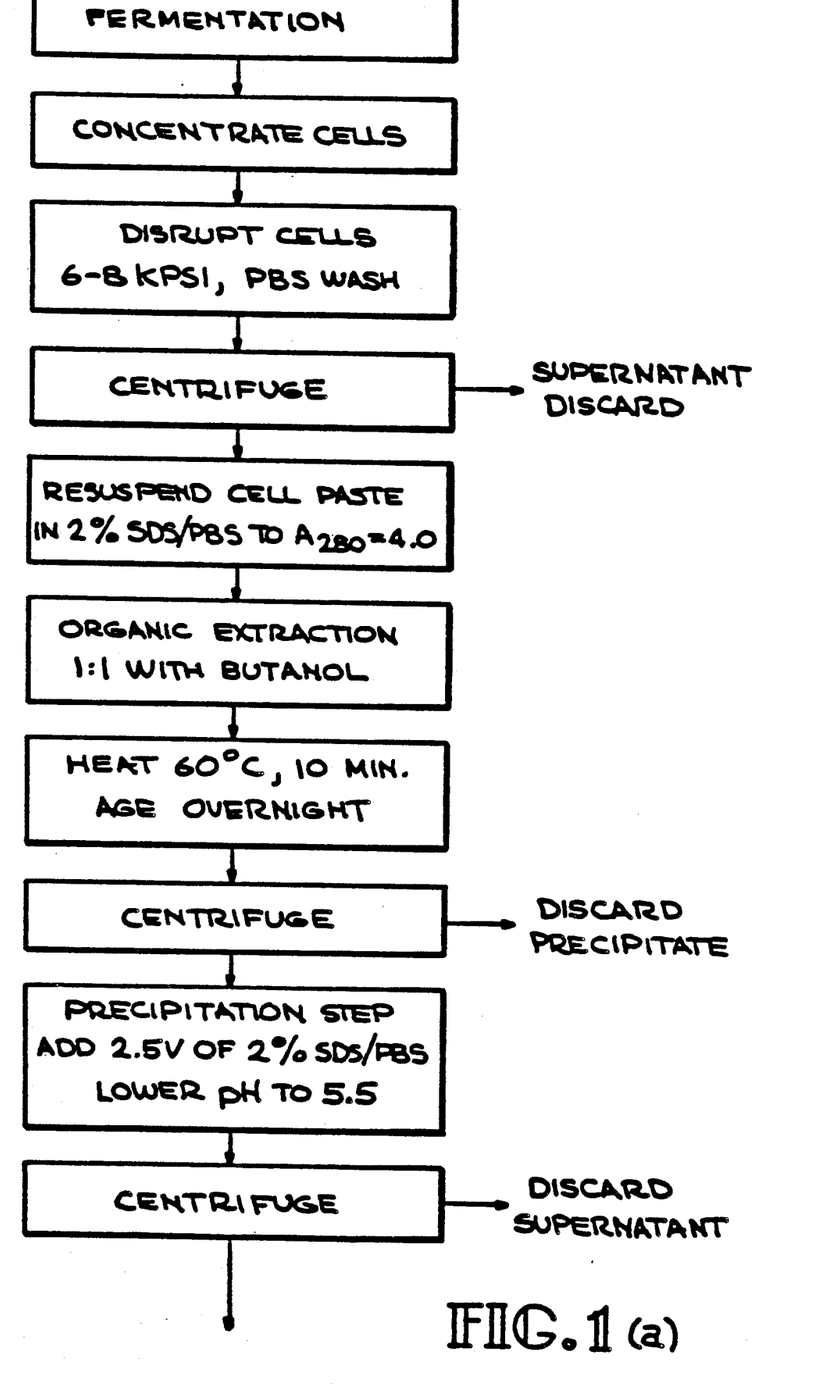
FIG. 1 illustrates a flow chart of the process steps of the present invention wherein the pH is raised to alkaline pH during diafiltration.
Figure 1B:
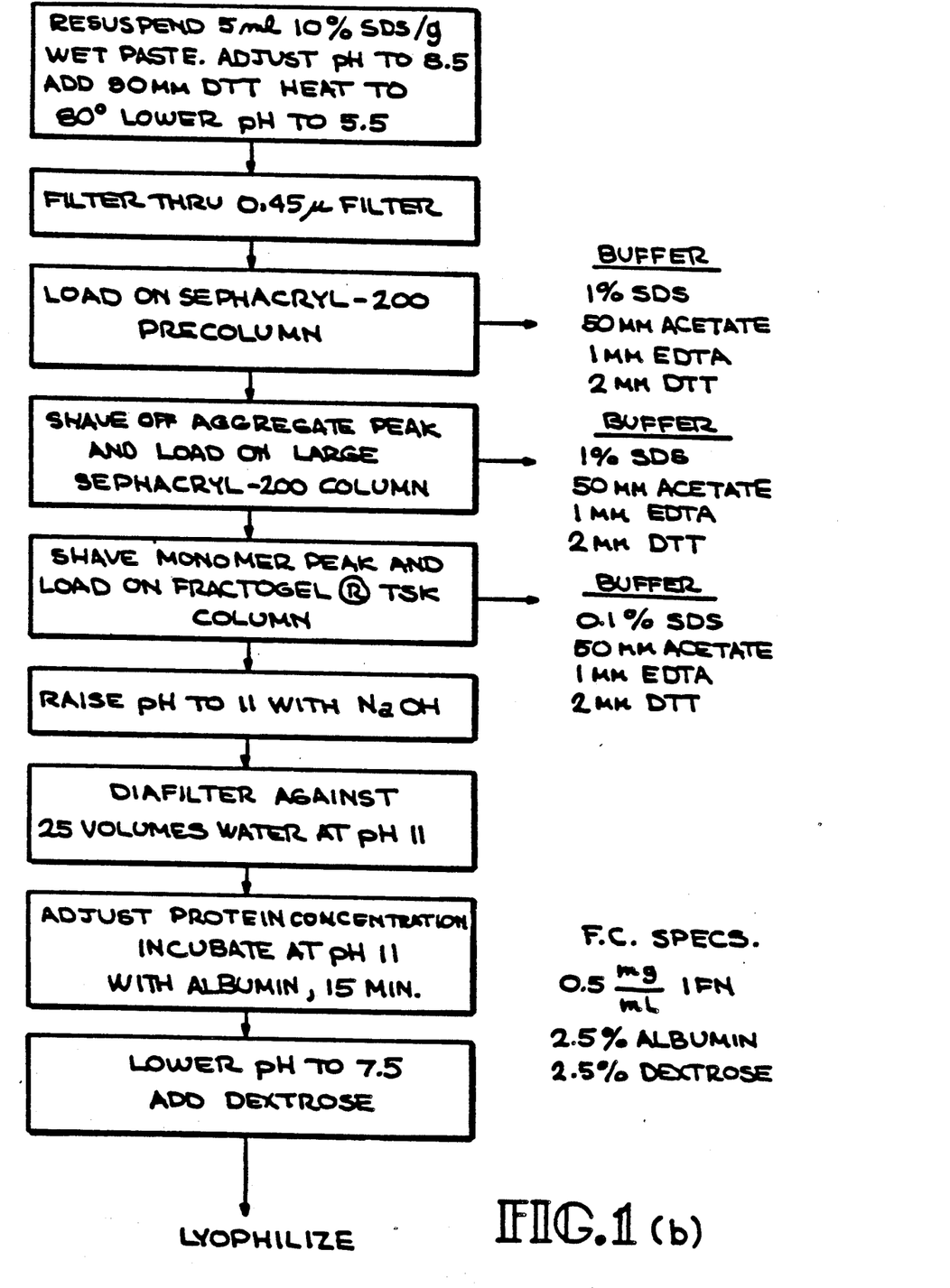
Figure 2:
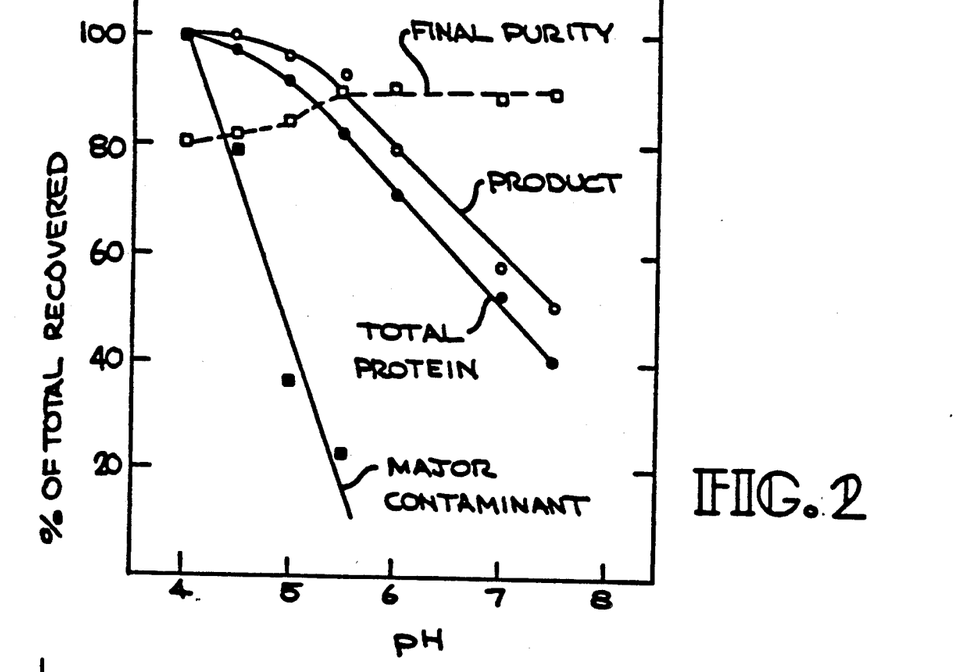
FIG. 2 shows a graph plotting percentage of the total recovery of recombinant human β-interferon and purity of the product during the precipitation step, as a function of pH in the range of about 4–8.

Upon completion of the extraction, the aqueous phase and extractant phase are separated and the protein is isolated from the extractant phase. The particular isolation procedure used depends upon the solubilizing agent involved and the desired degree of purity of the final product. Various isolation techniques such as precipitation, molecular sieve chromatography, affinity chromatography, and electrophoresis may be employed. In instances in which SDS is used, the desired lipophilic protein together with other proteins are precipitated from the extractant by mixing the extractant solution with aqueous buffer at volume ratios of about 2.0:1 to about 5:1, preferably about 3:1, and reducing the pH, typically to the range of about 5 to 7. The recovery of $\beta$-HIFN in the range of the pH 4 to 8, as shown in FIG. 2, shows a downward trend in the recovery of the protein with increasing pH, with an appreciable loss in the recovery of greater than 60% at a pH of about 8. Separation of the precipitate from the supernatant and evaporation of residual extractant from the precipitate provide a product that is greater than about 90% pure protein provided that the pH of the precipitation step is greater than 5.5. This product also contains minor amounts of nucleic acids ($<1\%$ to 2% by weight) and SDS ($<1\%$ w/v).

After further purification by methods known in the art, including but not limited to, chromatography, SDS may be removed in one embodiment of the invention by diafiltration at a pH of about 10.5 to 12.5, preferably about 12. The second purification step is optional and is not required for SDS removal by diafiltration. When sodium laurate is used as a solubilizing agent it precipitates from the extractant together with the protein on lowering the pH. Sodium laurate is extracted from the protein using organic solvents such as acetone, methanol and the like. Prior to diafiltration, the protein may be optionally reduced with appropriate reducing agents. Mercaptoethanol, glutathione, cysteine and dithiothreitol (DTT) may be employed for this purpose, with DTT being the most preferred.

The protein thus isolated is then solubilized in an aqueous-based carrier medium using a stabilizer as described above. The stabilizer, however, cannot merely be mixed with the protein for solubilization to occur. First the pH of the stabilizer must be raised to between 10.5 and 12.5 using a suitable base, preferably about 12, then the stabilizer is added to the diafiltered protein pool which is at pH 10.5-pH 12.5, and finally the pH of the resulting formulation is lowered to between about 6.8 and 7.8 Upon lowering the pH, the protein becomes solubilized in the medium.

Figure 5A:
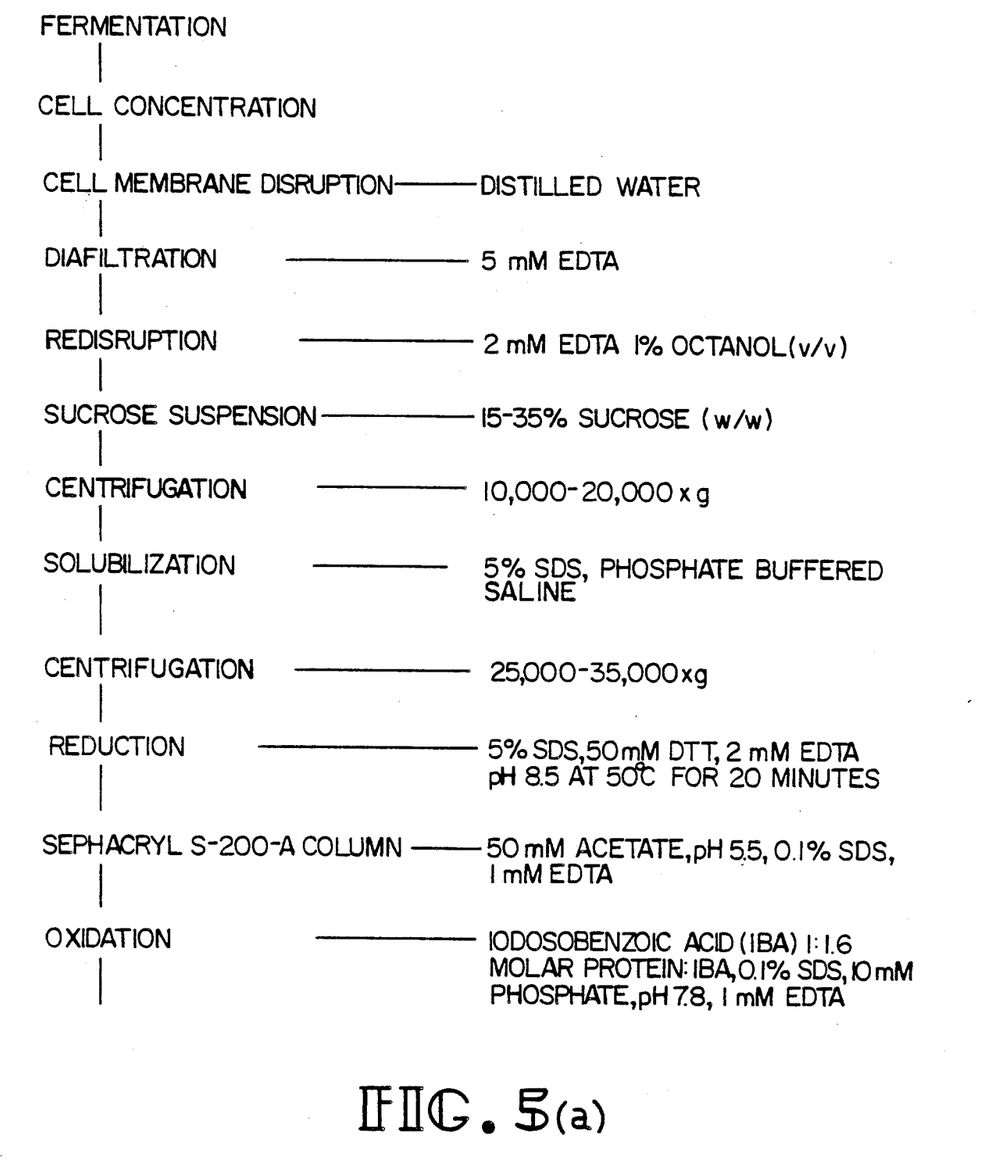
FIGS. 5a and 5b sequentially illustrate a flow chart of the process steps of the present invention wherein the protein is recovered from refractile bodies and the pH is lowered to acidic pH for stabilizer addition.
Figure 5B:
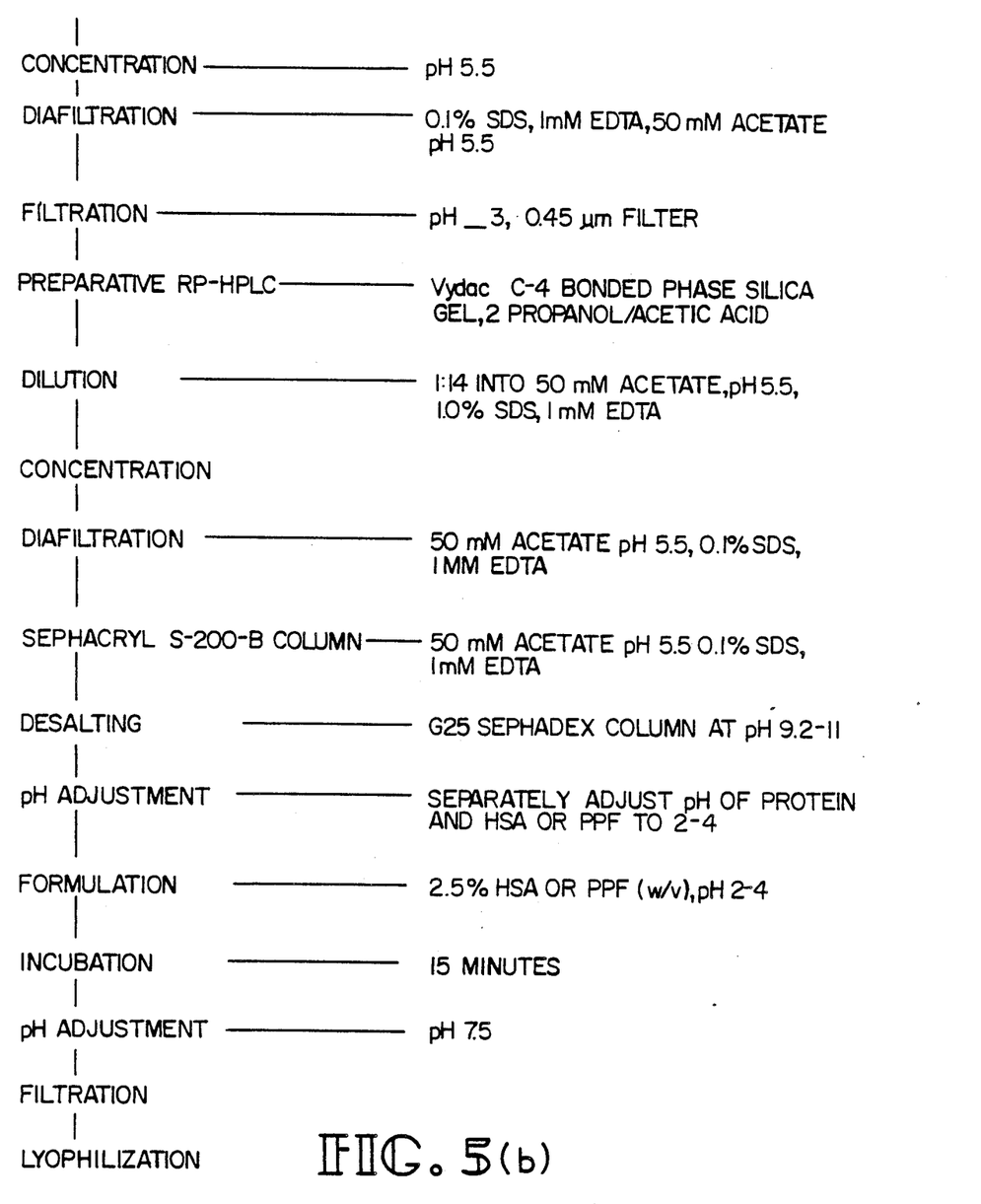

Another method for treating the disrupted cells is shown in FIGS. 5a and 5b, which is described in more detail in U.S. Pat. No. 4,748,234 issued May 31, 1988 which is a CIP of application Ser. No. 749,951 filed June 26, 1985, now abandoned, to Dorin et al., entitled "Process For Recovering Refractile Bodies Containing Heterologous Proteins From Microbial Hosts." The disclosure of this application is incorporated herein by reference. In this method the protein is extracted from refractile bodies and solubilized with a denaturing agent such as SDS. The SDS is later removed by a desalting column. The pH of the eluate is adjusted to 2 to 4, the pH of a stabilizer is adjusted separately to pH 2 to 4, the stabilizer is added to the eluate, the mixture is optionally incubated for generally about 10-100 minutes, depending on the factors described above, and the pH is adjusted to between 6.8 and 7.8.

In yet another method, shown in FIG. 6, the disruptate is extracted with a chaotropic agent, the protein is solubilized and reduced, and the reduced protein is separated, oxidized, purified and recovered. This method is described for IL-2 in U.S. Pat. No. 4,569,790 issued Feb. 11, 1986 entitled "Process For Recovering Microbially Produced IL-2", the entire disclosure of which is incorporated herein by reference. The formulation in FIG. 6 is obtained using a low pH adjustment procedure with an incubation period.

The carrier medium used for the formulation for therapeutic or clinical administration may be any non-toxic, inert and aqueous-based vehicle such as those commonly used to formulate pharmaceuticals for animal or human administration. The carrier also is selected so that it does not affect the biological activity of the lipophilic protein.

Examples of such carriers include distilled water, physiological saline, Ringer's solution, dextrose solution, and Hank's solution. The same carriers can be used to reconstitute lyophilized lipophilic protein.

The present invention is further described by the following examples. These examples are provided for purposes of illustration only and are not intended to limit the invention in any manner. In the examples all parts and percentages are by weight if solids and by volume if liquids, unless otherwise specified, and all temperatures are in degrees Celsuis.

EXAMPLE 1

Cell Production and Harvest

Human $\beta$-HIFN was recovered from *E. coli* that had been transformed to produce $\beta$-HIFN. The *E. coli* were grown in the following growth medium to a cell density (OD) of 10–11 at 680 nm (dry wt 10 g/l).

| Ingredient | Concentration |
|---|---|
| $NH_4Cl$ | 20 mM |
| $K_2SO_4$ | 16.1 mM |
| $KH_2PO_4$ | 7.8 mM |
| $Na_2HPO_4$ | 12.2 mM |
| $MgSO_4.7H_2O$ | 3 mM |
| $Na_3$ citrate.$2H_2O$ | 1.5 mM |
| $MnSO_4.4H_2O$ | 30 $\mu$M |
| $ZnSO_4.7H_2O$ | 30 $\mu$M |
| $CuSO_4.5H_2O$ | 3 $\mu$M |
| L-tryptophan | 70 mg/l |
| $FeSO_4.7H_2O$ | 72 $\mu$M |
| thiamine.HCl | 20 mg/l |
| tetracycline | 10 mg/l |
| glucose | 40 g/l |

The pH was controlled with $NH_4OH$.

The bacteria were then harvested and concentrated in a hollow-fiber cross-flow filtration system, using microporous polypropylene fiber system with an internal diameter (I.D.) of about 0.3 mm and a recirculation rate of about 3.5 gpm/cartridge.

EXAMPLE 2

Cell Disruption

The cells, at a final concentration of 9–10% (w/v), were mechanically disrupted by means of a Manton-Gaulin type homogenizer (Gray, P. P. et al., *IV IFS: Ferment Tech. Today* 347-351 (1972)), fitted with a special valve. A single pass at 6–10,000 psig pressure drop yielded greater than 90% cell disruption. The cells were subjected to three passes to obtain maximum disruption without losing $\beta$-HIFN activity and to shear nucleic acids to reduce viscosity.

EXAMPLE 3

Centrifugation Of Homogenate

The homogenized cell material was diluted 1:1 (v/v) with phosphate buffered saline (PBS) at a pH of about 7.4 to give a final volume of two liters. This material was continuously centrifuged at 12,000$\times$g at a flow rate of about 50 ml/min. The solid material was separated from the supernatant and resuspended in four liters of PBS containing two percent by weight of SDS. This suspension was stirred at room temperature for 15 minutes, after which there was no visible suspended material. The solution was then extracted with 2-butanol at a 1:1 volume ratio of 2-butanol to solution. The extraction was carried out in a liquid-liquid phase separator using a combined flow rate of about 200 ml/min. The organic phase was then separated and evaporated to dryness to yield 21.3 g of protein. This was resuspended in distilled water at a 1:10 volume ratio.

The recovered product was assayed for $\beta$-HIFN using an assay based on protection against viral cytopathic effect (CPE). The assay was made in microtiter plates. Fifty $\mu$l of minimum essential medium were charged into each well and 1:3 volume dilutions were made serially into the following wells. Virus (vesicular stomatitis), cell (human fibroblast line GM-2504), and reference $\beta$-HIFN controls were included on each plate. The reference $\beta$-HIFN was 100 units per ml. The plates were then irradiated with UV light for 10 minutes. After irradiation 100 $\mu$l of the cell suspension (1.2$\times$10$^5$ cells/ml) was added to each well and the trays were incubated for 18–24 hours. A virus solution at one plaque-forming unit per cell was added to each well except to the cell control. The trays were then incubated until the virus control showed 100% CPE. This normally occurred 18–24 hours after adding the virus solution. Assay results were interpreted in relation to the location of the 50% CPE well of the reference $\beta$-HIFN control. From this point the titer of interferon for all samples on the plate was determined. The activity of the recovered product was determined to be 2.9$\times$10$^6$ IU/mg.

EXAMPLE 4

Extraction of $\beta$-HIFN

A 10 liter tank was harvested (9.8 kg) and concentrated to 2.2 liters by cross-flow filtration. The slurry was frozen and stored for 34 days and then thawed.

The thawed concentrate was disrupted by three passes at 7$\times$10$^4$ kPa in a Manton-Gaulin type homogenizer. The disruptate was collected and made up to 4 liters with a solution of sodium laurate to give a final concentration of 1% w/v laurate. The pH was adjusted to 8.5 with 10% NaOH. The solution was contacted with a mixture of 50 vol % 2-butanol and 50 vol % 2-methyl-2-butanol in a static mixer. The emulsion was pumped into a holding tank and agitated to give a contacting time of 15 minutes. This emulsion was separated as described in Example 3 and the β-HIFN recovered in the organic phase. The activity recovered was 16% of the initial value with a specific activity (determined as in Example 3) of $3.7 \times 10^5$ IU/mg protein.

EXAMPLE 5

Acid Precipitation of β-HIFN

The process of Example 4 was repeated except that after extraction and separation of the aqueous and organic phases the organic phase was mixed with PBS or 10 mM phosphate buffer at a pH of about 7.4 at a volume ratio of 3:1. The pH of the mixture was lowered to about 5.5 by the addition of glacial acetic acid. The resulting precipitate was separated by centrifugation at 10,000–17,000×g for 15 minutes and the pellet was redissolved in 10% w/v SDS.

The precipitate was applied to a molecular sieve column with a Sephacryl S-200 ®Superfine matrix. The column was equilibrated with 50 mM sodium acetate buffer at pH 5.5 containing 2 mM DTT and 1.0% SDS (w/v). The column was developed with the same buffer at a flow rate of 5 ml per cm² per hour. Protein profile was monitored at 280 nm with a UV spectrophotometer. Fractions collected were assayed for protein content by methods known in the art. The interferon concentration was determined by the CPE assay as described in Example 3. Degree of interferon purity was determined by SDS polyacrylamide gel electrophoresis (PAGE). Fractions containing the highest interferon activities were pooled and the specific activity of the pooled interferon preparation was determined to be $1-2 \times 10^7$ IU/mg protein.

EXAMPLE 6

Final Chromatography

Figure 3:
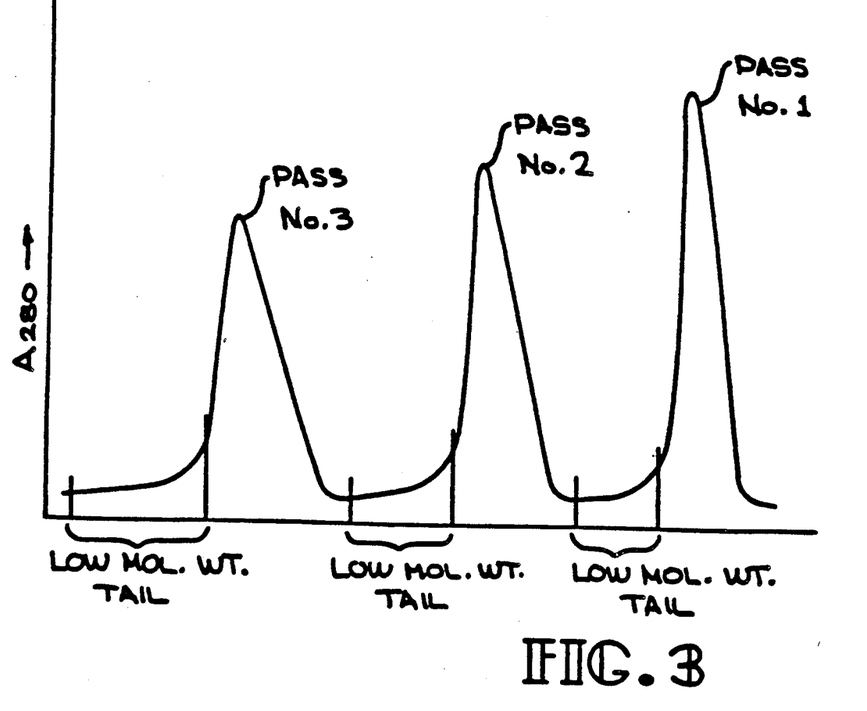
FIG. 3 is a representation of a chromatographic chart illustrating the homogeneity of the recombinant huran β-interferon fraction eluted after three passes through a vinyl polymer gel column.

The process of Example 5 was continued by concentrating the pool from the Sephacryl-200 step ten fold using a 10,000 nm wt. (nominal molecular weight) cut-off filter and then applying the material to a fine vinyl polymer gel column. This column was equilibrated with 50 mM sodium acetate buffer at pH 5.5 containing 2 mM dithiothreitol and 0.1% SDS (w/v). The column was developed with the same buffer at a flow rate of 15.6 ml/cm²/hr. The protein profile was monitored at 280 nm with a spectrophotometer, the protein peak was recycled three times prior to being collected, and fractions were assayed for protein activity and purity by SDS-PAGE. FIG. 3 depicts the eluate peaks after the first, second and third passes as monitored by the protein (β-HIFN) concentration plotted as O.D. vs. eluate fractions exhibiting protein absorption at 280 nm. The peak area after each pass remained substantially the same, indicating that there was no protein loss and that the preparation remained substantially homogeneous after three passes. Fractions containing the highest interferon assay by the cytopathic effect assay were pooled. Specific activity of the pool was in the range of $1-2 \times 10^7$ IU/mg protein.

EXAMPLE 7

Removal Of Residual Reagents

The pH of the pool collected in Example 6 above was raised to pH 12 and placed in a diafiltration device. This protein was reduced by treatment with 10 mM dithiothreitol (DTT) at pH 8.5 prior to raising the pH of the pool to 12 with 2.5 M sodium hydroxide. Reduction with DTT was optional and may be omitted if desired.

Figure 4:
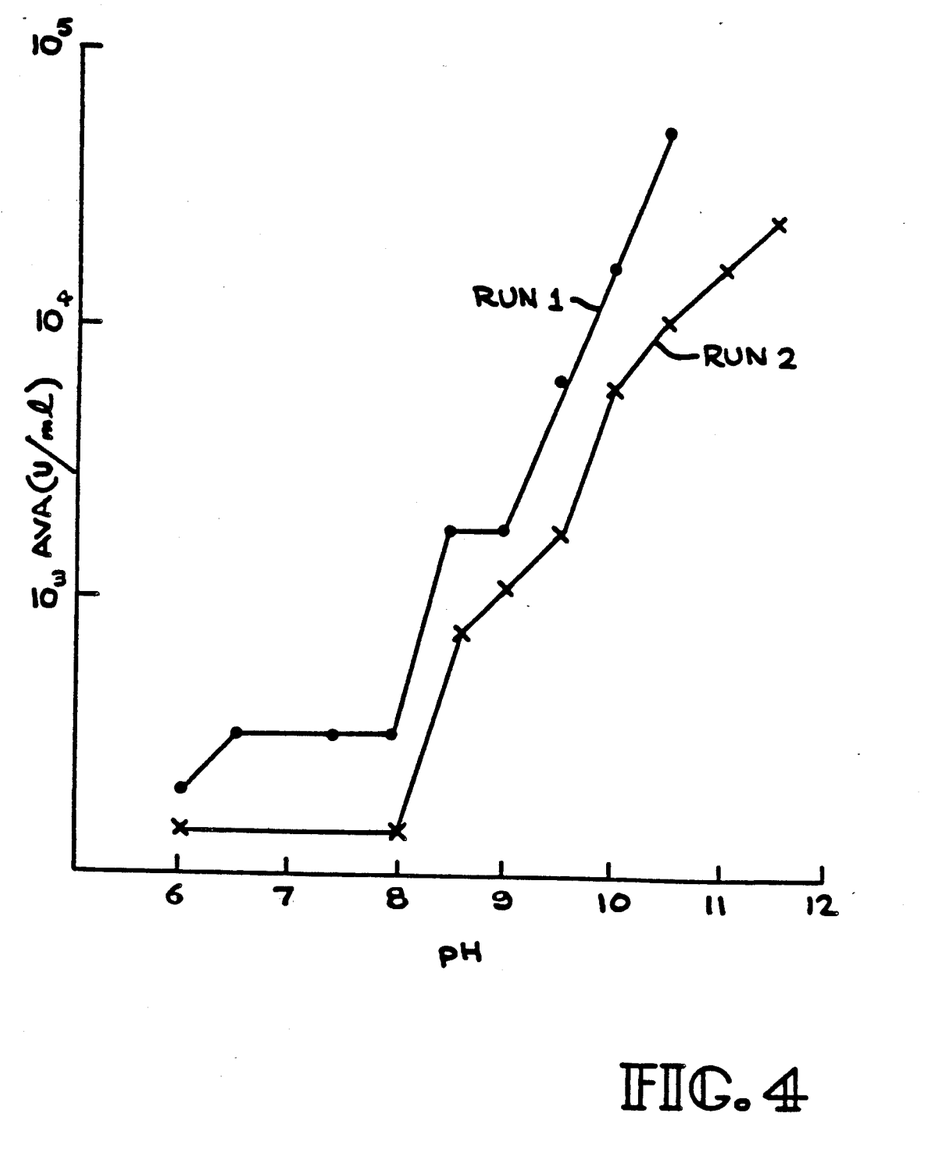
FIG. 4 is a plot of the antiviral activity of recombinant human β-interferon as a function of pH in the range of about 6–12.

Diafiltration was carried out at 1 mg/ml protein using a hollow fiber ultrafiltration cell equipped with a 1 sq. ft. surface area (10,000 dalton cut off) cartridge. The pool was diafiltered against 20 volume exchanges of water with the pH adjusted to 12 with 2.5 M sodium hydroxide. Sodium dodecyl sulfate levels were monitored and residual levels were found to be less than 10 p.p.m. Residual DTT, EDTA and other low molecular weight species were undetectable. The specific activity of the protein following diafiltration was unchanged from that prior to diafiltration. As shown in FIG. 4 the antiviral activity of β-HIFN following diafiltration was not lost even at a pH of 12.

EXAMPLE 8

Formulation With Human Serum Albumin/Dextrose

The diafiltered interferon (β-HIFN) from Example 7 was diluted to 0.25 mg/ml and incubated with pharmaceutical grade human serum albumin (final concentration 1.25% w/v.) for 15 minutes at pH 12. The pH of the solution was then lowered to 7.5±0.3 with dilute hydrochloric acid, and pharmaceutical grade dextrose was added to a final concentration of 1.25% w/v. The pool was then sterile filtered through an absolute 0.2 μm filter. Specific activity of the formulated material was $1-2 \times 10^7$ IU/mg interferon.

When 10% HSA at physiological conditions (pH 6.8 to 7.8) was added to the recombinant β-HIFN diafiltered concentrate from Example 7 which was at pH 11.5, the β-HIFN precipitated from the solution when the pH of the mixture was lowered to physiological pH. Only when the HSA and β-HIFN were both adjusted to pH 11.5 before mixing did the β-HIFN remain in solution when the pH of the formulation was reduced. Therefore, the formulation where recombinant β-HIFN is dissolved in the medium at pH 7.2–7.8 is obtained only by following a very specific pH adjustment procedure not previously known or disclosed.

In another experiment, β-HIFN with a serine residue substituted for a cysteine residue at position 17 prepared by the process described in U.S. Pat. No. 4,518,584 issued May 21, 1985 was purified on a G-75 Sepharose column. The G-75 pool comprised 50 mM acetate buffer at pH 5.5 containing 0.1% SDS and 1.88 mg/ml of the interferon. The actual concentration of SDS was 0.3–0.6 mg/ml. This pool was mixed in test tubes with 0.4, 0.8 or 1.2 ml of HSA. The final pH range of each formulation was 6.8–7.2, and the same results would occur if the final pH were increased up to 7.8. In each case the interferon precipitated from the formulation. Therefore, the lipophilic protein cannot merely be mixed with HSA as a stabilizer at a pH of 6.8–7.8.

EXAMPLE 9

Lyophilization And Reconstitution

The sterile formulated interferon pool was filled in 4 ml aliquots and lyophilized using the following cycle.

1. Product at −35° C., <100 millitorr for at least 1 hour.
2. Product at −20° C., <100 millitorr for at least 1 hour.
3. Product at +25° C., <100 millitorr for at least 4 hours.

The vials were then sealed under 10″ Hg vacuum.

The product was reconstituted in distilled water for injection to either 0.5 mg IFN/ml or 1 mg IFN/ml. Specific activity of the product corresponded to 0.9–1×10⁷ IU/mg β-HIFN.

The current formulations are lyophilized and reconstituted as follows:

The sterile formulated lipophilic protein pool is filled in vials of 1–15 ml aliquots and lyophilized as follows. The product is frozen for a minimum of two hours at −30° C. A chamber containing the product vials is then evacuated to <100 millitorr and the product is held for at least 16 hours at −30° C., followed by a 12° C. ramp per hour to 15° C. The product is held at 15° C. for a minimum of 10 hours.

The vials are then sealed under 10 inches Hg vacuum.

The product is reconstituted in distilled water for injection of from 0.25 to 0.75 mg/ml of lipophilic protein. Specific activity of IL-2 is 2–4×10⁶ IU/mg and of IFN-B is 1.8×10⁸ IU/mg.

EXAMPLE 10

IFN-$\beta_{ser17}$ is a microbially produced mutein of IFN-$\beta$ in which the cysteine residue at amino acid position 17 is replaced with a serine residue. IFN-$\beta_{ser17}$ has two remaining cysteine residues: one at position 31 and the other at position 141. In native IFN-$\beta$ the cysteines at positions 31 and 141 interact to form a disulfide bridge. The genetically engineered *E. coli* strain used in this example to produce IFN-$\beta_{ser17}$ was deposited in the American Type Culture Collection, 12301 Parklawn Drive, Rockville, Maryland 20852 USA on Nov. 18, 1983 under accession number 39,517.

The genetically engineered *E. coli* mentioned above was grown in the following medium:

| Ingredient | Approximate Initial Concentration |
| --- | --- |
| Na₃ Citrate.2H₂O | 3 mM |
| H₂PO₄ | 30 mM |
| (NH₄)₂SO₄ | 74 mM |
| MgSO₄.H₂O | 3 mM |
| MnSO₄.H₂O | 46 μM |
| ZnSO₄.7H₂O | 46 μM |
| CuSO₄.5H₂O | 1–2 μM |
| L-tryptophan | 350 μM |
| FeSO₄.7H₂O | 74 μM |
| thiamine.HCl | 0.002% (w/v) |
| glucose | 0.5% (w/v) |

A 25% solution of Dow Corning Antifoam B, a 50% solution of glucose and 5N KOH were added on demand.

The temperature was maintained at 37°±1° C., the pH at 6.5±0.1 with NaOH, and dissolved oxygen at 30% w/w of air saturation. Optical density and residual glucose measurements were taken at 14 hours and at approximately one-hour intervals thereafter. Harvest was made when glucose consumption reached 40±6 g/l (OD at 680 nm=10–11).

The harvested material was concentrated approximately 3-fold by circulating it through a microporous cross-flow filter under pressure. The concentrated cells were diafiltered against deionized water until the harvest material was concentrated 4–5 fold. The cells were then disrupted by passing them through a Manton-Gaulin homogenizer at 4.1–5.5×10⁴ kpa (0.6–0.8 psi). After the initial pass sodium dodecyl sulfate (SDS)-sodium phosphate buffer was added to a final concentration of 2% w/v SDS, 0.08 M sodium phosphate, and solubilization was continued for one hour. Solid dithiothreitol (DTT) was then added to a final concentration of 50 mM and the homogenate was heated to 90±5° C. for 10 minutes. The resulting cell suspension was extracted with 2-butanol at 1:1 2-butanol:suspension volume ratio in a static mixer. The mixture was then centrifuged and the 2-butanol-rich phase was collected.

The 2-butanol-rich phase was mixed with 2.5 volumes of 0.1% w/v SDS in phosphate buffered saline (PBS). Solid DTT was added to a final concentration of 1 mM. The pH of the mixture was adjusted to 6.2±0.1 with glacial acetic acid and this mixture was centrifuged. The resulting paste was collected and resuspended in a mixture of PBS and 10% w/v SDS with pH adjustment to 8.5±0.1 using 1N NaOH. Solid DTT was added to a final concentration of 100 mM and the suspension was heated to 90°±5° C. for 10 minutes. The suspension was then cooled to about 25° C., the pH was adjusted to 5.5±0.1 with glacial acetic acid, and the solution was filtered.

The solution was then applied to a Sephacryl S-200 precolumn with a buffer consisting of 1% SDS, 50 mM sodium acetate, 1 mM EDTA, pH 5.5. The fractions containing highest interferon activities were pooled and concentrated by ultrafiltration with a 10 kilodalton molecular weight cut-off.

The protein was oxidized to generate sulfhydryl bonds using the method of Shaked, et al., supra. A 1 mM o-iodosobenzoic acid solution was prepared by mixing the acid in water, sonicating the mixture for about five minutes and then stirring and adding 2% NaOH slowly to obtain a final pH of 8.2±0.2 (additional sonication may be used as an alternative to adding base).

A reaction buffer medium was prepared by dissolving Na₄P₂O₇·10H₂O in water to a concentration of 2 mM. The pH of this solution was adjusted to 9.0 by adding 10% acetic acid, SDS to 0.1%, and ethylenediaminetetraacetic acid (EDTA) to 1 mM and the o-iodosobenzoic acid solution to 15 μM were added to the solution.

The buffer medium was placed in a reaction vessel equipped with a magnetic stirrer and a pH electrode set at 9.0. The IFN-$_{ser17}$ preparation and the o-iodosobenzoic acid solutions were added to the reaction mixture from holding vessels using peristaltic pumps that were calibrated to introduce equivalent mole ratios of the IFN and oxidizing agent. The pH of the reaction mixture was controlled at 9.0 by adding 0.25 M NaOH via a peristaltic pump at 5 ml/hr as needed. The IFN-$\beta$ solution (5 mg/ml in 50 mM acetate buffer, pH 5.5) was added at a flow rate of 2 ml/hr (7.0 micromole/hr) for about five hours; the o-iodosobenzoic acid solution was added at 7 ml/hr (7 micromole/hr) over the same time period. The addition of the acid solution was continued thereafter to get a final excess of 10–15 micromolar. The reaction was followed by reverse phase HPLC and by assaying the residual thiol content of IFN-$\beta_{ser17}$ by Ellman's assay. After 6.5 hours the reaction was terminated by adding 10% acetic acid to the reaction mixture to a pH of 5.5.

The product was then loaded on a Sephacryl-200 column using a buffer consisting of 0.1% SDS, 1 mM EDTA, and 50 mM sodium acetate at pH 5.5. The monomer peak from this column was pooled and loaded on a Sephadex G-75 column using a buffer consisting of 0.1% SDS, 1 mM EDTA, and 50 mM sodium acetate at pH 5.5.

I. PPF Formulation

A total of 1.3 mg/ml of IFN-β from the G-75 pool was loaded on a desalting G25 Sephadex column equilibrated with a pH 11 buffer. A total of 2.2% plasma protein fraction (PPF) was adjusted to pH 3 and added to 5.56 ml of the desalted IFN-β, containing 0.25 mg/ml IFN-β. PPF is derived from Cohn Fraction $IV_1$. PPF is similar to HSA with the exception that PPF has more α- and β-globulins. Fraction $IV_1$ has the highest amount of α and β globulins. The IFN-β and PPF mixture was incubated for about 45 minutes and then adjusted to pH 7.5. The resulting mixture was visually clearer than the pH 12 HSA IFN-β formulation described above.

II. PPF/HSA Formulations

A total of 30 ml of the G-75 IFN-β pool above was concentrated to 10.5 ml and the pH was adjusted to 11. The concentrate was desalted on a G25 Sephadex column fully equilibrated to pH 11. The IFN desalted pool was used in the following experiments:

A total of 3.33 ml of the desalted IFN-β having 0.25 mg IFN per ml was used in each experiment and the pH of each mixture was adjusted to 3 before incubation and adjusted to between 7.3 and 7.5 after incubation. The results are indicated in the table below.

| Stabilizer | Amount of Stabilizer (%) | Incubation Time (min.) | Clarity at pH 7.3–7.5 |
|---|---|---|---|
| HSA | 2.5 | 45 | slightly hazy |
| HSA | 5.0 | 45 | very clear |
| HSA | 2.5 | 15 | slightly hazy |
| HSA | 5.0 | 15 | very clear |
| PPF | 2.5 | 45 | very clear |
| PPF | 2.5 | 15 | very clear |

The PPF formulations were found, when examined visually, to have the best clarity, with 5.0% HSA next best, followed by 2.5% HSA. When each formulation was lyophilized and reconstituted with water, the PPF formulations reconstituted more clearly than the HSA formulations. All lyophilized formulations had IFN-β activity.

Experiments done at pH 3–4 without an incubation period appeared to show no appreciable difference from those that undergo an incubation period. Changes in concentration of PPF do result, however, in a marked difference in clarity.

EXAMPLE 11

Des-ala IL-$2_{ser125}$ is an IL-2 whose amino acid sequence differs from native human IL-2 by: (1) the absence of the initial N-terminal alanine residue and (2) a serine substituted for cysteine at position 125. The strain of des-ala IL-$2_{ser125}$-producing *E. coli* used for this example was deposited in the ATCC on Mar. 6, 1984 under accession number 39,626.

The genetically engineered *E. coli* mentioned above the grown in a fermenter using the following growth medium:

| Initial Ingredients Added | Approximate Initial Concentration |
|---|---|
| $(NH_4)_2SO_4$ | 72 mM |
| $KH_2PO_4$ | 21.6 mM |
| $Na_3$ Citrate | 1.5 mM |
| $ZnSO_4.7H_2O$ | 60 μM |
| $MnSO_4.H_2O$ | 60 μM |
| $CuSO_4.5H_2O$ | 2 μM |
| pH adjusted to 6.50 with 2.5 N NaOH | |
| Autoclaving | |
| Sterile Additions (post autoclave) | |
| $MgSO_4.7H_2O$ | 3 mM |
| $FeSO_4$ | 100 μM |
| L-tryptophan | 70 mg/l |
| Thiamine-HCl | 20 mg/l |
| Glucose | 5 g/l |
| Tetracycline | 5 mg/l |
| Ethanol (optional) | 2% (w/v) |
| Casamino acid | 2% (w/v) |

A 20% solution of Dow Corning Antifoam B, a 50% solution of glucose and 5 N KOH were added on demand.

The pH of the fermenter was maintained at 6.8 with 5N KOH. Residual glucose was maintained between 5–10 g/l, dissolved oxygen at 40% w/w, and temperature at 37°±1° C. The casamino acids (20% w/v stock solution) were added when the $OD_{680}$ was about 10–15. Three hours after adding the casamino concentrated solution, ethanol (95% w/w) was added to achieve a final 2% w/w concentration. Harvest was made two hours after ethanol addition.

About 20–40 g (wet weight) of the *E. coli* MM294-1 cells containing the induced, cloned IL-2 were resuspended in 200 ml of 50 mM Tris, 1 mM EDTA (pH 8.1 to 8.5) The high pH aided in selective extraction of *E. coli* proteins in subsequent steps. The cells were centrifuged at 3000–4000×g for 10 minutes and resuspended in 200 ml of Tris/EDTA buffer at 4° C.

The cells were then sonicated at 4° C. for 45 minutes (or until the optical density at 600 had dropped about 85%) using large probe pulsing with 50% duty on power setting "9" of Heat Systems Model W-375 sonicator. Alternatively the cells were broken by three passes through a Manton-Gaulin homogenizer. The homogenate was centrifuged at 4500×g for 10 minutes (6000 rpm) using a Beckman JA20 rotor at 4° C. The debris was resuspended in 50 ml of a Tris/EDTA mixture at room temperature. Over a period of five minutes an equal volume of 8M urea (Schwartz/Mann ultra pure) in Tris/EDTA buffer was added to the suspension with rapid stirring to yield a final urea concentration of 4M. The resulting mixture was stirred slowly for 15–30 minutes at room temperature.

After stirring, the mixture was centrifuged at 12,000×g for 15 minutes (12,000 rpm in Beckman JA20 rotor at room temperature) and the pellet was saved. The pellet was then resuspended in 9 ml of 50 mM sodium phosphate (at pH 6.8), 1 mM EDTA, 10 mM DTT at 20° C. The pellet was then solubilized by addition of 1 ml of 20% w/v SDS and vortexed vigorously. The resuspension was centrifuged at 12,000×g for 10 minutes at room temperature and the insoluble material was discarded.

The remaining solution was heated to 40° C. for 15 minutes to ensure that all of the IL-2 was fully reduced. The supernatant fluid (containing 40% pure IL-2) was loaded onto a 2.6 cm×100 cm Sephacryl-S-200 column run in 50 mM sodium phosphate (pH 6.8) 1 mM EDTA, 1 mM DTT, 1% w/v SDS. Then 3 μl aliquots of each fraction were run on a 15% w/v SDS/PAGE minigel and the gel was stained with Coomassie blue. The fractions with the fewest contaminants (minimizing the inclusion of contaminants at about 35 K, 18 K and 12 K daltons) were pooled and concentrated to 5-10 ml using an Amicon YM5 ultrafilter. The preparation was about 80-90% pure IL-2.

The S-200 pool was loaded onto a 2.6 cm × 100 cm Sephadex G-100 column, which was eluted as described above using 0.1% w/v SDS. The fractions were analyzed by SDS/PAGE and the purest fractions pooled. These purest fractions contained 95-98% pure IL-2 with 0.2-0.5 ng of endotoxin per 100,000 units. Over 30% of the IL-2 present in the crude lysate was recovered as pure IL-2.

When stored at 4° C. under nitrogen these pooled G-100 fractions were found to be stable for at least six weeks without additions. An SDS-containing precipitate formed at 4° C. which could be redissolved at 25° C. prior to use or could be removed without significant loss of IL-2 units.

The purified, fully reduced product obtained as described above was oxidized using iodosobenzoic acid as described above, resuspended, and run on an HPLC column using propanol-trifluoroacetic acid. Formulations were made from the HPLC pool.

I. Low pH Treated Mannitol and HSA Formulations

The HPLC pool was then concentrated and diafiltered versus a buffer (Buffer K) of 50 mM acetate, 1 mM EDTA and 0.1% SDS. About 30 mg of the diafiltrate was concentrated and diafiltered versus 10 mM Tris.HCl at pH 9.2. Ten mg of this diafiltrate was loaded on a G-25 desalting column to remove SDS to a level of 0.65 μg/mg. Sufficient acid was added to the G-25 pool to reduce its pH to 3, and it was split into three portions. To the respective portions was added sufficient amounts of stabilizer to yield the following final formulation concentrations: 5% (w/v) mannitol, 1.25% (w/v) human serum albumin (HSA), and 2.5% (w/v) HSA.

The 2.5% HSA formulation was split into two portions, one of which was incubated for 30 minutes and one of which was incubated for 60 minutes. Both 2.5% HSA samples were clear after incubation. The pH of both was raised to 7.5 with 2.5 N NaOH with no change in the clarity, indicating solubility.

A. Low pH Treated HSA Formulation

The above HSA formulation experiment was prepared in a larger volume to test visual clarity. The same IL-2 was diafiltered in Buffer K versus Tris HCl at pH 9.2. This material was then concentrated and loaded on a desalting G25 Sephadex column. To a total of 49.6 ml IL-2 from the desalted pool (60 ml final volume) was added 100 μl of 6 N HCl to adjust the pH to 2.58. To 5.9 ml of 2.5% HSA and 4.5 ml H$_2$O was added dropwise concentrated HCl to a pH of 3. The IL-2 solution was incubated with the albumin solution for 15 minutes at pH 3, and then the pH was raised with 2.5 N NaOH to 7.5. The solution was clear, indicating that the IL-2 dissolved in the solution at physiological pH. After lyophilization and reconstitution with water the sample remained clear.

It is apparent that this method of desalting removes considerable SDS. Increasing the HSA concentration from 1.25 to 2.5% resulted in considerable improvement in solubility at physiological conditions, indicating that higher concentrations of stabilizer are preferred for low pH treatments whereas for the higher pH treatment, above pH 10, 1.25% HSA results in very good solubilization.

B. Low pH Treated Mannitol Formulation

A mannitol IL-2 formulation was prepared by mixing 49.6 ml of the G-25 desalted IL-2 pool described just above in Section A with 15 ml of 25% mannitol and adjusting the pH of the mixture down to 3.0 with HCl. The final concentration of mannitol was 2.5% (w/v). After lyophilization and reconstitution with water the sample remained clear at pH 3.0.

This example illustrates that the stabilizers herein can be used to stabilize the formulation at a low pH of 2-4 if the pH is maintained at 2-4 and lyophilization at pH 2-4. If the pH is raised above 4, however, the carbohydrate stabilizers such as mannitol will not act to solubilize the lipophilic protein. Only the protein stabilizers such as HSA will solubilize the protein as the pH is raised to physiological pH.

II. Low pH Treated PPF Formulation

The same desalted IL-2 pool as used above for HSA formulation was employed containing 1 μg/ml IL-2 at pH 9.2. When 7.5 ml PPF (5%) and 2.5 ml of 1 μg/ml of the desalted IL-2 were mixed, the mixture had a pH of 7.6 and was clear at first, but within two minutes turned hazy. When the pH of the mixture was dropped to 2.3 after 15 minutes, it was clear and remained clear when the pH was readjusted to 7.5.

In a second case, the pH of 7.5 ml of 5% PPF was adjusted to 9.2, and Tris HCl at pH 8.8 was added (0.05 μl of 1.5 M). A total of 2.5 ml of 1 μg/ml desalted IL-2 as described above was added and the mixture was incubated for 15 minutes at pH 9.2. When the pH was dropped to 7.6, the solution was clear, but after one minute it began to turn slightly hazy.

In a third case, when the pH of the 5% PPF was lowered to 3.1, IL-2 at pH 3.3 was added, the mixture was adjusted to pH 3.1 with dropwise concentrated HCl, the mixture was incubated for 15 minutes, and the pH was raised with 2.5 N NaOH, the resulting solution was as clear as the control formulation (3.75% PPF alone).

Comparison of formulations with 2.5% HSA, 2.5% PPF, 0.5% HSA and 0.5% PPF (w/v) under identical conditions revealed that HSA formulations are clearer than PPF formulations, but both types of formulations are acceptably clear, indicating suitable solubility.

The low pH formulation was found not to be as soluble as the pH 12 formulation. Experiments to optimize the pH 3 formulation revealed that 5% HSA was distinctly better than the 2.5% HSA formulation. Also, increasing the incubation time from 15 minutes to 60 minutes assisted the solubility. The 5% HSA at 15 minutes incubation, however, was found to be better than the 2.5% HSA at 60 minutes incubation.

The above results indicate that for IFN-β, PPF is a better stabilizer than HSA, whereas for IL-2, HSA is a better stabilizer than PPF. In addition, tests for biological activity of representative formulated proteins at pH 3 revealed that the proteins were biologically active.

The process and compositions of the present invention as described herein yield a lipophilic protein preparation which is of relatively high purity, with residual SDS levels of less than about 10 p.p.m. and which may be formulated into therapeutically acceptable preparations in a non-toxic, inert, physiologically compatible carrier medium for clinical and therapeutic uses. The principal advantage of the instant invention lies in the reduction of SDS levels in the protein preparation (which can potentiate hepatic toxicity in some patients) to about 2-20 p.p.m., preferably to less than about 10 p.p.m., and more preferably to about 2-6 p.p.m., which are therapeutically acceptable. Although the preferred embodiment described relates to β-HIFN and IL-2 specifically, the purification methods of the instant invention can be used to purify other proteins with similar lipophilic characteristics to β-HIFN and IL-2.

The foregoing description of the preferred embodiments of the instant invention has been presented for purposes of illustration and description. It is not intended to be exhaustive or to limit the invention to the precise form disclosed, and obviously many modifications and variations are possible in light of the above teaching. The particular embodiments were chosen and described to explain best the principles of the invention and its practical application thereby to enable others skilled in the art to utilize best the invention in various embodiments and with various modifications as are suited to the particular use contemplated. It is intended that the scope of the invention be defined by the claims appended hereto.

What is claimed is:

1. A stable pharmaceutical composition suitable for human clinical use comprising a therapeutically effective amount of a biologically active unglycosylated recombinant interleukin-2 (IL-2) protein wherein said IL-2 is at least about 95 % pure as determined by SDS/PAGE and contains endotoxin in the amount of less than 0.5 ng per 100,000 units of IL-2 activity and wherein said IL-2 is solubilized in a non-toxic, inert therapeutically compatible aqueous-based carrier medium at a pH of 6.8 to 7.8 comprising human serum albumin.

2. A composition according to claim 1 wherein the medium is at a physiological pH.

3. A composition according to claim 1 wherein any sodium dodecyl sulfate present in the medium is present at levels of less than 10 ppm.

4. A composition according to claim 3 wherein the level of said sodium dodecyl sulfate present in the medium is from about 2 to 6 ppm.

5. A composition according to claim 1 wherein the protein is produced from a bacterial host.

6. A composition according to claim 1 wherein said human serum albumin is present in an amount of 0.1 to 5%.

7. A composition according to claim 1 wherein said human serum albumin is present in a concentration range of about 0.5 to 10%.

8. A composition according to claim 1 wherein said effective amount are in the range of 0.1 to 1 mg IL-2 per ml of said carrier.

* * * * *